United States Patent [19]

Allart et al.

[11] Patent Number: 4,759,357
[45] Date of Patent: Jul. 26, 1988

[54] PODIATRIC ORTHESIS FOR ORIENTATION OF THE CALCANEUS AND SUBTALAR BONES

[76] Inventors: Gérard Allart, 995 Myrand, Ste Foy, Quebec, Canada, G1V 2W1; Luc R. Albert, 1440 de Lantagnac, Sillery, Quebec, Canada, G1T 2E6

[21] Appl. No.: 7,660

[22] Filed: Jan. 28, 1987

[51] Int. Cl.⁴ .............................. A61F 5/14; A43B 7/14
[52] U.S. Cl. ..................................... 128/581; 128/584; 128/586
[58] Field of Search ............... 128/581, 585, 586, 583, 128/584

[56] References Cited

U.S. PATENT DOCUMENTS

| 545,006 | 8/1895 | Baird | 128/581 |
|---|---|---|---|
| 730,366 | 6/1903 | Gunthorp | 128/581 |
| 1,335,981 | 4/1920 | Morton | 128/581 |
| 2,903,802 | 9/1959 | Pochynok | 128/581 |
| 3,148,678 | 9/1964 | Roberts | 128/80 D |
| 3,545,447 | 12/1970 | Silverman | 128/583 |
| 3,997,984 | 12/1976 | Hayward | 128/621 X |
| 4,216,778 | 8/1980 | Weiss | 128/581 |
| 4,232,457 | 11/1980 | Mosher | 128/595 X |
| 4,266,553 | 5/1981 | Faiella | 128/585 |
| 4,325,380 | 4/1982 | Malkin | 128/581 |
| 4,442,612 | 4/1984 | Hauser | 36/43 |
| 4,503,576 | 3/1985 | Brown | 36/43 |
| 4,513,518 | 4/1985 | Jalbert et al. | 128/619 X |
| 4,520,581 | 6/1985 | Irwin et al. | 128/595 X |
| 4,571,857 | 2/1986 | Castellanos | 128/595 X |
| 4,572,196 | 2/1986 | Prahl | 128/581 |
| 4,597,196 | 7/1986 | Brown | 128/581 X |
| 4,689,898 | 9/1987 | Fahey | 128/586 |

Primary Examiner—Edgar S. Burr
Assistant Examiner—Tonya Lamb
Attorney, Agent, or Firm—Robic, Robic & Associates

[57] ABSTRACT

A podiatric orthesis for the tridimensional plantal development of the foot of a patient, which orthesis is conceived according to medical anatomical standards. It comprises a base having a rear part in the shape of a cupola, dimensioned for adapting to the calcaneus, and a median part projecting forwardly of and as an extension of the rear part. The latter is designed to hold the vertical axis of the calcaneus coaxial with the axis of the leg. The bottom of the cupola rises forwardly at an angle of about 30° with respect to the ground to orient the calcaneus forwardly and at the same angle. The longitudinal axis of the rear part is oriented toward the fifth metatarsus of the foot so as to likewise orient the calcaneus. The median part has an inner border which concavely curves to support the subtalar.

8 Claims, 6 Drawing Sheets

Fig. 16

TABLE 1

| SIZE → | | 23 | 24 | 25 | 26 | 27 | 28 | 29 | 30 | 31 | 32 | 33 | 34 | 35 | 36 | 37 |
|---|---|---|---|---|---|---|---|---|---|---|---|---|---|---|---|---|
| WIDTH ↓ | SUBTALAR HEIGHT → | | | | | | | | | | | | | | | |
| 7E | 1 | | | | | | | | | | | | | | | |
| | 2 | | | | | | | | ▨ | | | | | | | |
| | 3 | | | | | | | | | | | | | | | |
| 3E | 1 | | | | | | | | | | | | | | | |
| | 2 | | | | | | | | ▨ | | | | | | | |
| | 3 | | | | | | | | | | | | | | | |
| BCD | 1 | | | | | | | | | | | | | | | |
| | 2 | | | | | | | | ▨ | | | | | | | |
| | 3 | | | | | | | | | | | | | | | |

PODIATRIC ORTHOSIS FOR ORIENTATION OF THE CALCANEUS AND SUBTALAR BONES

BACKGROUND OF THE INVENTION

1. Field of the invention

The present invention relates to a podiatric orthesis for tridimensional plantar development. It is adapted to be inserted into a shoe or to be directly incorporated in the internal sole of a shoe in order to actively correct faults in the tridimensional axialization of the bones of the foot or to assist in the correct development of normal feet, in young children or in adolescents.

2. Development of the invention

Extensive observations and research work carried out by the present inventors have, quite surprisingly, revealed to them certain clinical signs, such as:

bronchial spasms, progressive appearance of astigmatism and short sightednesss, pains in the knees in children, after three hours of sleep, dyslexis, dysgraphies, weakness in visuo-manuel association and lateralization, child refusing or retarding to walk past the age of 16 or 18 months, pains or fatigue of the musculo-skeleton type of overlying mobile segments, frequent headaches, lack of balance when standing on one foot.

All or part of the above syndromes may be directly associated with the growth of the feet and more specifically to a fault in tridimensional axialization of the bones of the feet and, namely, the calcaneus and the subtalar.

This weakness in axialization may in practice reside in a collapse of the plantar arch; a faulty axialization of the calcaneus with respect to the axis of the leg or with respect to the fifth metatarsal.

These anomalies are respectively called: flat foot, heel varus or valgus and inverted feet.

PURPOSE OF THE INVENTION

The object of the present invention is to provide the practitioner with an orthesis which is especially designed not only for remedying the aforesaid operational problems resulting from a weakness in plantar equilibrium but also for promoting a corrective growth of the foot and for preventing deformations of the foot likely to appear in growing children. This object is achieved by acting on the triple axialization of the calcaneus and of the subtalar in a manner capable of ensuring a correct and complete physiological growth of the child.

More specifically, the orthesis according to the invention is designed so as to properly position the skeleton of the foot without freeing it from muscular effort. It thus becomes possible to restore completely the normal tridimensional axialization of the foot bones after a period of muscular reeducation.

DESCRIPTION OF THE PRIOR ART

Most of the orthesis known today are designed solely for supporting the plantar arch. For this purpose, the known orthesis comprises at least one full and internal half cupola over which the said plantar arch comes to rest. Such supports, by holding passive the bones of the feet, limit the action of the plantar muscles which thus progressively lose all their tonicity.

The use of this type of orthopedic sole by persons presenting a collapsed plantar arch does in no way allow reeducation of the muscles in order that they may thereafter ensure by themselves holding of the foot bones in normal position. These soles constitute, at the most, an element of comfort for walking.

Nevertheless, certain orthopedic soles are presently known that areintended to reeducate the plantar arch. Thus U.S. Pat. No. 4,216,778 discloses an orthopedic sole conceived to restore the normality of the skeletal arch, without providing a support to the plantar arch, in order not to hinder the muscular function. This sole is also designed to try to correct other deformations of the foot skeleton. However, regarding the structure of this sole, no reference is made in the patent to medical anatomical standards, scientifically defined and commonly called "The canons of the foot".

Furthermore, this orthopedic sole is entirely made of rigid synthetic resin, agreeing with the generally accepted notion that a holding structure which is rigid is essential for the proper support of the foot.

Going against accepted concepts, the present inventors believe that such stiffness impedes the mobility of a moving foot and, as a consequence, the reeducation possibility of such an orthopedic sole is reduced.

The orthopedic sole, according to the above U.S. patent is obtained by molding of the deficient foot, disposed by the practitioner in a neutral position having to correspond to the correct position of a normal foot carrying the weight of the body distributed from the heel to the toes.

As a consequence, such a manner of proceeding is subject to the hazards of a subjective and approximate manipulation resulting in a probably inadequate orthesis. In addition, it does not have any development trend, neither it seems to be industrially oriented.

SUMMARY OF THE INVENTION

In order to remedy the aforesaid disadvantages, the present invention proposes an orthesis of which the structure is defined with precision, according to the "canons of the feet", in such a manner either to provide an efficient correction of tridimensional axialization faults in the calcaneus and in the subtalar, or to ensure a normal development of the walking process in growing children.

More specifically, the invention relates to a podiatric orthesis for the tridimensional plantar development of the foot of a patient and conceived according to anatomical and medical standards, the orthesis comprising:

a base having a rear part in the form of a cupola dimensioned for adapting to the calcaneus of the said foot and a median part projecting forwardly of and as an extension of said rear part; said rear part being designed to hold the vertical axis of the calcaneus coaxial with the axis of the patient's leg;

wherein said rear part has a bottom which is forwardly and upwardly uprighted according to an angle of about 30° with respect to the ground whereby to orient the calcaneus in the said forward direction and according to the said angle;

wherein said rear part has a longitudinal axis oriented in the direction of the location of the distal tip of the fifth metatarsus of the said human foot whereby to orient the calcaneus in the said direction; and wherein said median part is formed with an inner border concavely curving so as to wind around the plantar arch of the patient.

Besides, this orthesis is made in one piece and so that its rear part be rigid or semi-rigid, to hold the calcaneus firmly in normal 90° position, relative to the ground, and so that its front part be flexible. It is profiled so that it follows the shape of the foot in order to avoid hurting it and also to respect the function and effort of the plantar muscles so that the latter fully accomplish their function of upholding the arch skeleton in their normal axial plantar position.

In other words, by associating together a good muscular tonicity and a proper tridimensional axialization, it is possible to improve the mechanics of the feet during walking cycles of the children and to promote a better perception of the external world.

Further advantages and features of the invention will appear from the description that follows of a preferred embodiment of the invention having reference to the appended drawings.

BRIEF DESCRIPTION OF THE DRAWINGS

FIG. 16 is a reference table illustrating the possible industrial making of a set of tridimentional ortheses for the growing and developing feet of children, in all width and size of orthopedic shoes, following the actual industrial standards.

DESCRIPTION OF THE PREFERRED EMBODIMENT

In order to understand the present invention better, it appears appropriate first to describe the skeleton of the foot with regard to its structure and its function.

Figures 1, 2:
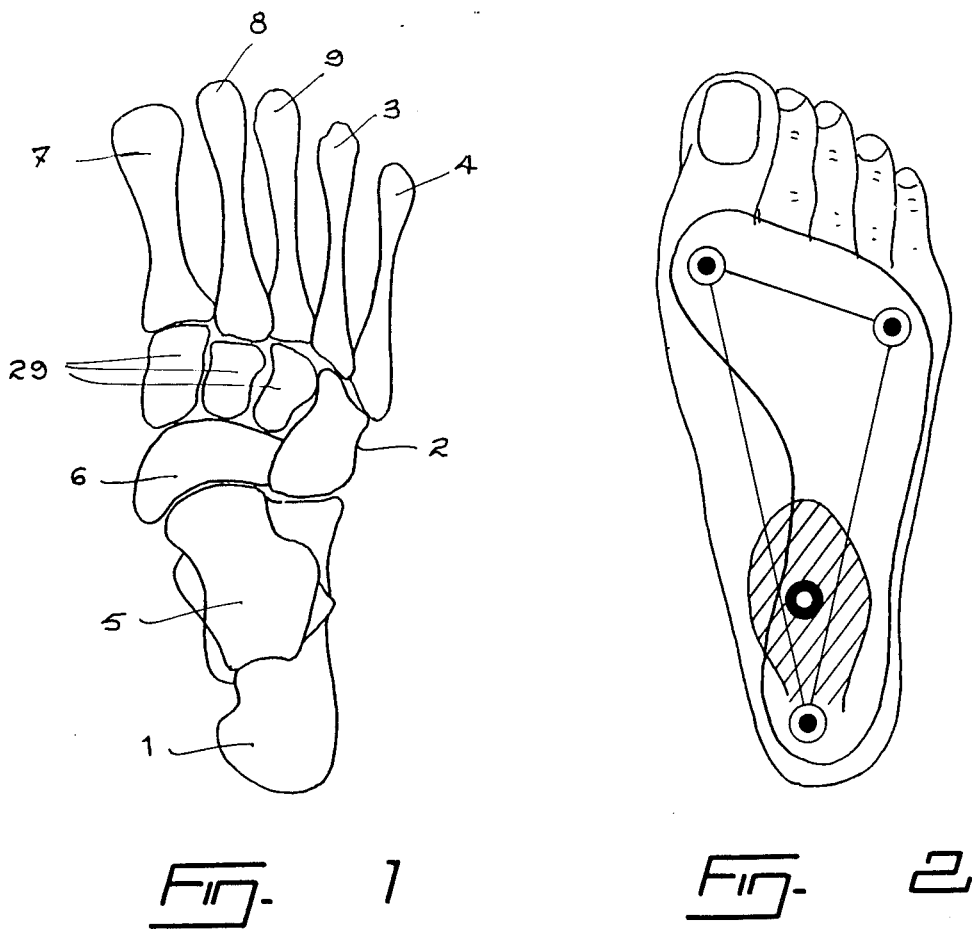
FIG. 1 is a diagrammatic view of a normal foot skeleton.
FIG. 2 is a diagrammatic view of the foot, illustrating the support triangle.

As shown in FIG. 1, a foot may be considered to be axially divided into two parts:

the calcaneus or external foot of which the function is that of static support during walking. It is made up of the calcaneus 1, the cuboid 2, and the fourth and fifth matatarsus 3 and 4;

the subtalar or internal foot which has a dynamic function which is complementary to that of the calcaneus foot; this function appears in motion during the evolution of the step; it is made up of the subtalar 5, the scaphoid 6, the cuneiforms 29 and the first three metatarsus 7, 8 and 9.

Figure 4:
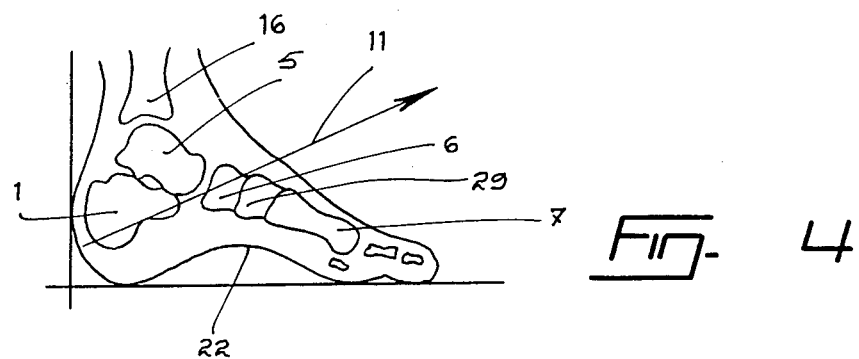
FIGS. 4 and 5 are sagittal views, respectively of a normal foot and of a flat foot.

As shown in the sagittal view of FIG. 4, the calcaneus 1 is the starting point of the inner longitudinal skeletal arch. It is generally admitted that the longitudinal inner axis 11 of the calcaneus 1 makes an angle of 30° with the horizontal, looking forwardly.

Figure 5:
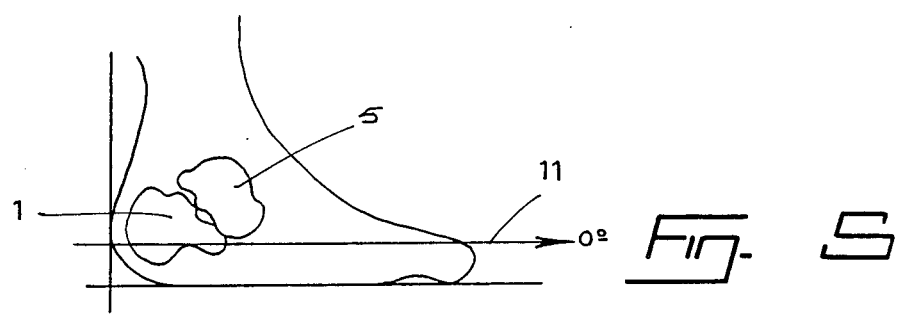

In the case of a flat foot, this angle is less than the 30° required under normal physiological conditions, as shown in FIG. 5.

Figure 8:
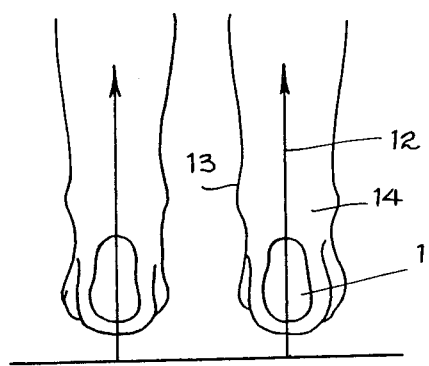
FIGS. 8, 9 and 10 are posterior frontal views of, respectively, a normal foot; a heel varus foot and a heel valgus foot.
Figures 9, 10:
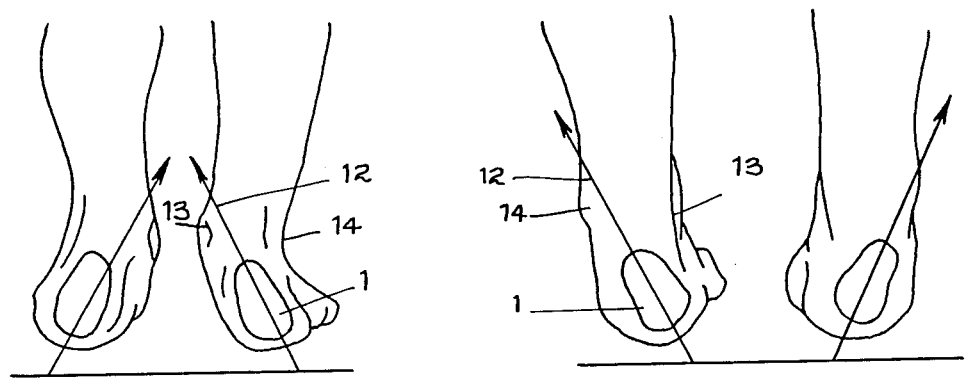

Viewed from the frontal rear plane of FIG. 8, the calcaneus 1 has the shape of a trapezium of which the bisector 12, under normal physiological conditions, must coincide with the bisector of the leg. Where this is not so, the result is a heel Valgus deformation or a heel Varus deformation, depending on the bisector 12 leaning inwardly toward the inner ankle face 13, as in FIG. 9 (Varus) or outwardly torward the outer ankle face 14, as in FIG. 10 (Valgers).

Figure 13:
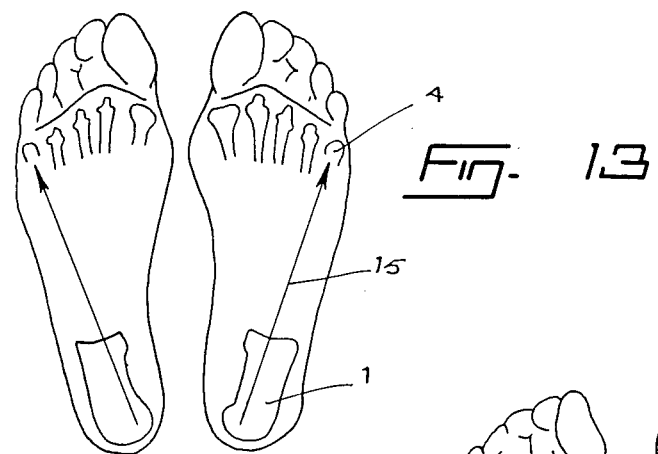
FIGS. 13 and 14 are, respectively, plantar viaws of a normal foot and of an inverted foot.
Figure 14:
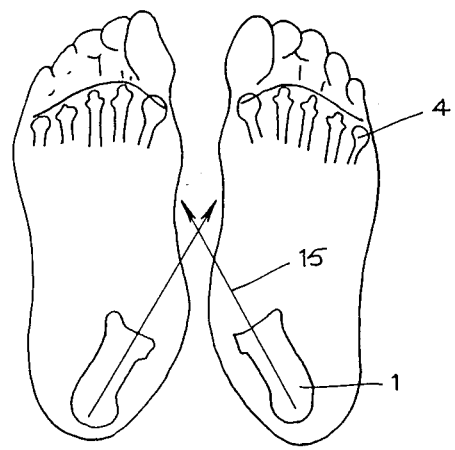

Viewed from the plantar plane of FIG. 13, the bisector 15 of the calcaneus 1 must be directed toward the distal tip of the fifth metatarsus 4. A deviation of the bisector 15 inwardly of the foot, as in FIG. 14 is called an inversion deformation of the foot.

As FIG. 4 illustrates, the subtalar 5 which is located between the tibia 16, the calcaneus 1 and the scaphoid 6, acts as a "pulley" transmitting the weight of the body in motion and distributing it adequately on the three immediate supporting points of the foot which form a sustentation triangle, shown in FIG. 2, within which the line of force coming from the leg must end up, under normal conditions.

The subtalar 5 being the bone which is immediately associated with the calcaneus 1, axial offsetting (desaxialization) of the latter causes that of the subtalar 5. The latter may then no longer exercise its function of transmission and distribution of the pressure properly and this results in a plantar unbalance.

In order to appropriately correct all of the axialization faults of the calcaneus mentioned above or to ensure that a growing foot develops normally, the orthesis of the present invention must provide various means each adapted to correct a specific defect. The orthesis may, additionally comprise means to support the subtalar, considering the important role of the latter in the mechanical structure of the foot.

Figure 3:
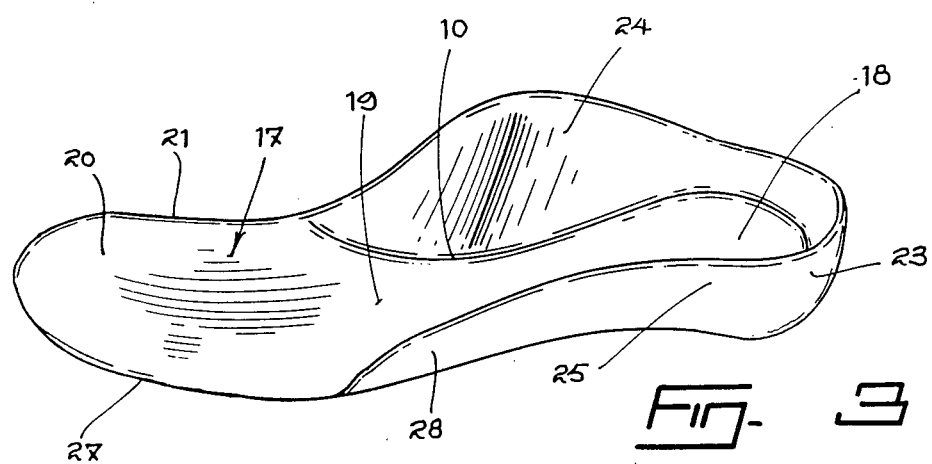
FIG. 3 is a perspective view of an orthesis made according to the invention.
Figure 15:
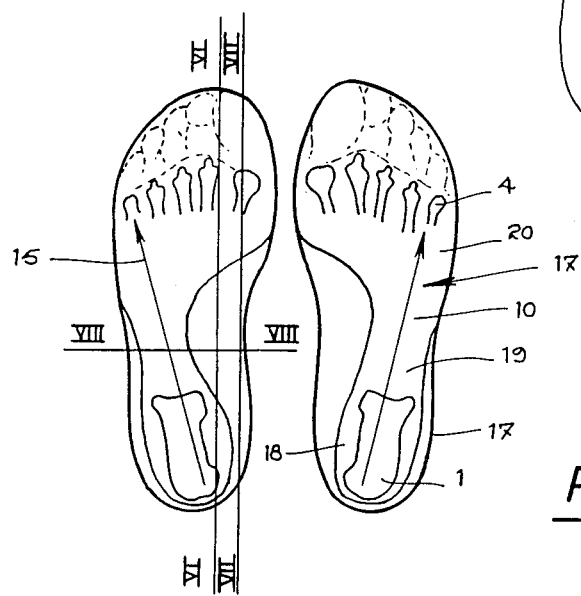
FIG. 15 is a plantar of the orthesis of FIG. 3.

Viewed from the plantar plane of FIG. 15, the orthesis according to the invention as shown in perspective in FIG.3, is made in one piece and comprises a base 17 including three parts:

a rear part 18 corresponding to the position of the calcaneus 1;

a median part 19, corresponding to the position of the subtalar 5, being an extension of the rear part 18;

a front part 20, corresponding to the position of the metatarsus and of the toe bones, being an extension of the median part 19.

This base 17 has contours that are adapted to the shape of the foot of the patient and an inner edge 21, FIG. 3, which curves in a concave manner at the level of the median part 19 so as to follow the plantar arch 22 (FIG. 4).

Figure 12:
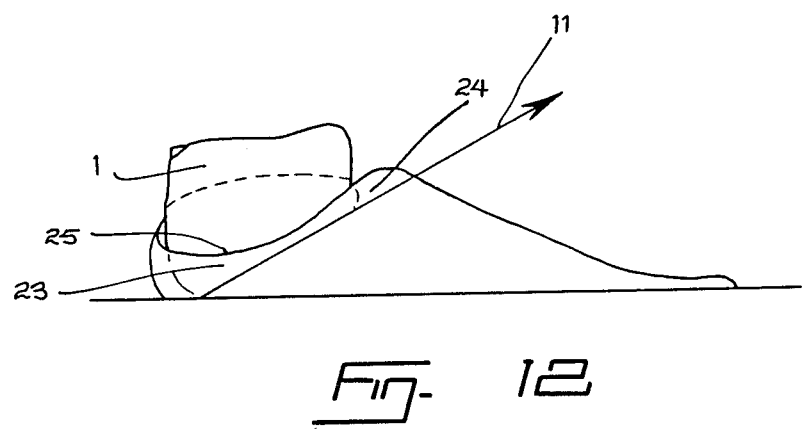
FIG. 12 which appears on the same sheet of drawings as FIG. 7a, is a diagrammatic longitudinal view of the internal side of the orthesis.
Figure 11:
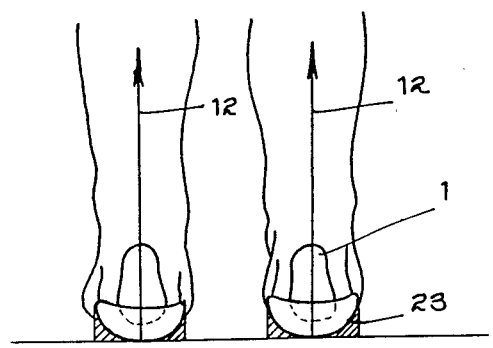
FIG. 11 is a posterior frontal view of the orthesis of FIG. 3.

Viewed from the rear frontal plane, FIG. 11, the rear end of the orthesis has the shape of a cupola 23 designed to adapt itself to the shape of the heel. This calcaneus cupola 23, having a depth corresponding to ⅓ of the height of the calcaneus 1, includes all of the base of the latter, as is also illustrated in FIG. 12.

The borders of the cupola 23 have, as a prime function, to neutralize any lateral shifting of the calcaneus 1 (heel Valgus or Varus) and reestablish proper axial alignment of the axis 12 of the calcaneus with the axis of the leg (see FIG.11).

Figure 6:
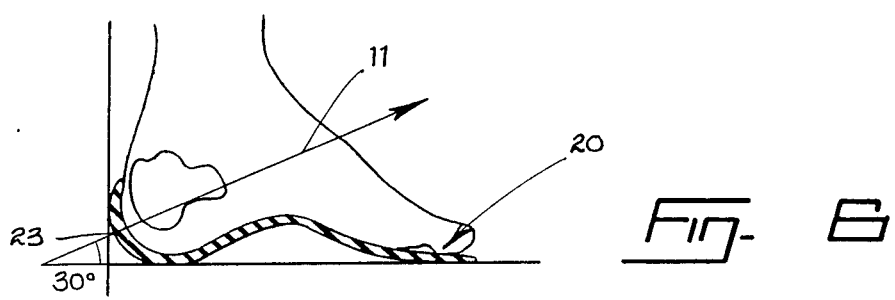
FIGS. 6 and 7 are sagittal views of the orthesis of FIG. 3, respectively along lines VI—VI and VII—VII of FIG. 15.

Viewed from the sagittal plane of FIG. 6, the rear end 23 of the orthesis has the form of a slope curving from the lower rear extremity of the calcaneus 1 up to the upper front extremity of the same bone, along an oblique slope 11 of 30°.

This thus rearwardly rocked slope orients the calcaneus forwardly according to a 30° angle with respect to the ground, notable in normal feet. This allows restoration of the curve of the plantar arch 22 which is inexistant in the case of flat feet (see FIG.4).

Figure 7:
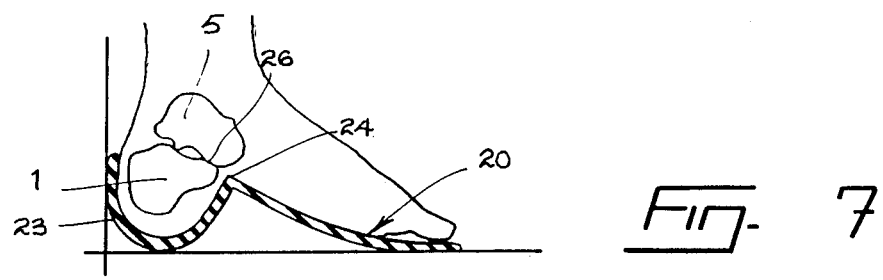
Figure 7A:
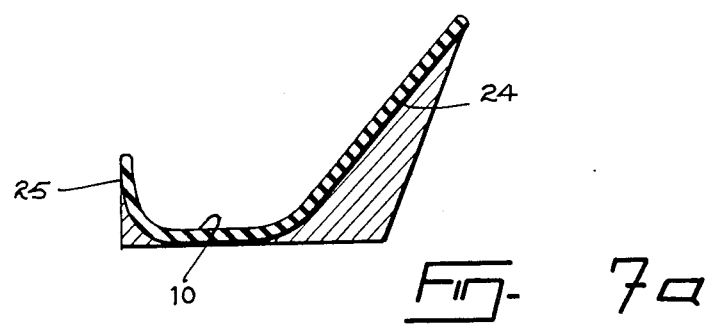
FIG. 7a is a cross sectional view along line VIII—VIII of FIG. 15.

On this same 30° slope, starting from one third the inner upper front extremity, is added a wedged structure 24 as an extension over the inner face of the peripheral edge 25 of the cupola 23 (see FIG.7).

FIG. 7 illustrates that this wedged structure 24 rises upwardly, in the median portion 19, (FIG. 3) along the concave inner edge 21 in such a way that the tip comes to support the inner front lower part of the subtalar 5.

This subtalar support is namely essential when the foot turns Valgus. Indeed, the subtalar 5 of a foot having this type of deformation tends to be shifted toward the inner side of the foot. Consequently, the subtalar support 24 has been designed so as to hold the subtalar in the normal longitudinal axis but it must in no way be confused with a plantar arch support.

Referring to the plantar plane of FIG. 15 again, the axis 15 of the calcaneus cupola 23 is oriented toward the location of the fifth metatarsus 4, that is toward the front external edge of the orthesis. This direction corresponds to the normal physiological orientation of the calcaneus 1.

Such a cupola 23 thus permits correcting deviations in the axis of the calcaneus that are observed in a pathological inversion of feet.

As illustrated in FIG. 3, the median part 19 of the base 17 extends upwardly on the outer edge 27 to form a longitudinal border 28 which thereby constitutes a continuous forwardly directed extension of the peripheral edge 25 of the calcaneus cupola 23. The height of the border 28 gradually decreases from the cupola 23 until it dies out at the forward end of the median portion 19.

It will be noted, as a consequence and from FIGS. 3 and 15, that the calcaneus cupola 23 is extended by a longitudinal passage 10 constituted centrally by the median part 19 of the base 17 and laterally delimited by the outer border 28 and the support structure 24 of the subtalar 5. The axis of the passage 10 mingles with that of the calcaneus cupola 23 and, starting from the forward third, the passage 10 flattens out in the forward direction and widens in the direction of the inner edge 21.

The passage 10, by thus winding around the plantar arch, leaves it free of any support. In normal physilogical conditions, this orthesis has, as a function, to avoid any compression on the nerves and vessels that travel through the plantar arch. Narrowing of the orthesis, in its median part 19, thus respects the blood circulation and does not affect muscular functioning.

The orthesis according to the invention is made so that the calcaneus cupola 23 be rigid or semi-rigid in order to hold the calcaneus in normal position and in such a manner that the front part be supple from the 25/40th of the length of the foot measured from the rear edge along the longitudinal bisector 15 and according to a transverse line making an angle of 45° with the bisector 15 at the point previously defined, in an outer-rear-/inner front orientation.

Such orthesis are capable of being made of polymeric materials, synthetic or natural.

The shape of the orthesis appropriate to the dimensions of a particular foot and respecting the anatomical and medical standards may be obtained by conventional graphic methods and its realization calls for known handicraft processes. The methods namely call for three defined conventional parameters which are: the size, the width of the foot measured at one third from the front end and the subtalar height (that is the height, measured from the ground, of the lower inner and forward part of the subtalar).

Conventionally, the making of an individual orthesis requires the use of known craftsman processes. However, orthesis made in that manner are costly by reason of their manner of manufacture.

A method of industrially making an orthesis according to the invention resides in industrially making, in a first step, a set of orthesis intended to fill all particular needs of a certain clientele. The process of obtaining them involves the following steps:

to design the shape of at least one orthesis, for which the size, the width of the foot and the subtalar height are defined; this shape being established from anatomical and medical standards;

to manually make at least one prototype of this or these orthesis, and to obtain, from the said orthesis and by means of a calibrating machine, the set of orthesis that are sought for.

Thereafter, molds are made of the set of orthesis initially obtained so as to manufacture, by thermo-injection, the orthesis intended for the clientele.

By way of a non-limitative example, the table of FIG. 16 gives a set of orthesis intended for a child clientele, comprising orthesis of sizes varying from 23 to 37; each size being represented in three foot-widths 7E, 3E and BCD, as well as in subtalar heights nos: 1, 2 and 3, for a total of 135 ortheses of different sizes, widths and heights. This set may be realized from designated by the following parameters:

(a) size 30, width 7E, subtalar height no. 2,
(b) size 30, width 3E, subtalar height no. 2,
(c) size 30, width BCD, subtalar height no. 2.

What is claimed is:

1. An one-piece podiatric orthesis conceived according to anatomical and medical standards for the tridimensional plantar development of the foot of a patient, said orthesis acting simultaneously on both the calcaneus and subtalar of said patient's foot and comprising:

(a) a rear part in the form of a cupola open at a forward end thereof, said cupola being designed and dimensioned for adapting to the calcaneus of the patient's foot and including:

a cupola bottom wall having a rear edge, and inner edge and an outer edge, said cupola bottom wall being forwardly and upwardly uprighted according to an angle of about 30° with respect to the ground whereby to orient the calcaneus in the said forward direction and according to the said angle; and a cupola peripheral border extending upwardly from said bottom wall along the rear, outer and inner edges thereof with respect to said patient's foot, said cupola peripheral border having inner and outer portions corresponding to said inner and outer edges, said inner and outer portions being so shaped and oriented as to (i) neutralise any lateral shifting of the calcaneus and permanently reestablish proper axial alignment of the vertical axis of the calcaneus with the axis of the patient's leg, and simultaneously (ii) orient the longitudinal axis of the calcaneus in the direction of the fifth metatarsus of the patient's foot, (b) a median part projecting forwardly of and as an extension of said rear part, said median part including:

a median part bottom wall disposed in the continuation of said cupola bottom wall and having inner and outer edges; and an inner border upwardly extending along the inner edge of said median part bottom wall, said inner border of said median part continuously extending the inner portion of said cupola peripheral border, and (c) a wedged structure defining a wedge tip for supporting and holding the subtalar of the patient's foot, said wedged structure being located at the level of said median part on the inward side of said orthesis and consisting of an integral extension of the inner border of said median part rising up to such a height as to reach and laterally sustain the inner, lower and forward part of the subtalar.

2. An orthesis according to claim 1, wherein the outer portion of the cupola peripheral border is essentially straight adjacent the open end of the cupola;

the inner portion of the cupola peripheral border is bent toward the outer edge of the cupola bottom wall; and the inner border of the median part is curved concavely so as to wind around the plantar arch of the patient.

3. An orthesis according to claim 2, wherein said rear part in the form of a cupola is made of rigid material and said wedged structure is made of supple material.

4. An orthesis according to claim 2, wherein the median part further includes an outer border upwardly extending along the outer edge of said median part, said outer border being a straight continuation of the outer border of said rear part and having a height gradually decreasing in the forward direction and from said periphery.

5. An orthesis according to claim 2, wherein said rear part in the form of a cupola has a depth corresponding to about one third of the height of the calcaneus.

6. An orthesis according to claim 2, further comprising:

(d) a front part made of supple material, said front part projecting forwardly of and as an extension of said medium part and being located in correspondence to the metatarsus and toe bones of the patient's foot.

7. An orthesis according to claim 6, wherein said front part made of supple material starts from 25/40 th of the foot length as calculated from the rear edge thereof, said cupola being made of plastic material sufficiently rigid to hold the said calcaneus in normal position.

8. An orthesis according to claim 7, wherein said rigid and supple materials separate along a line inclined at about 45° with respect to the longitudinal axis of said cupola in an outer-rear and inner-front orientation with respect to said cupola.

* * * * *